United States Patent
Zapata Penasco et al.

(10) Patent No.: US 10,309,951 B2
(45) Date of Patent: Jun. 4, 2019

(54) BIOREACTOR FOR THE IN SITU STUDY OF MICROBIAL BIOFILMS INDUCING CORROSION ON METAL SURFACES

(71) Applicant: INSTITUTO MEXICANO DEL PETROLEO, Mexico City (MX)

(72) Inventors: Norma Icoquih Zapata Penasco, Mexico City (MX); Vicente Garibay Febles, Mexico City (MX); Florentino Leyte Guerrero, Mexico City (MX); Ubaldo Sadott Pacheco Y Alcala, Mexico City (MX); Jorge Alberto Mendoza Perez, Mexico City (MX); Jesus Emmanuel Juarez Rojo, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 220 days.

(21) Appl. No.: 15/241,640

(22) Filed: Aug. 19, 2016

(65) Prior Publication Data
US 2017/0052165 A1    Feb. 23, 2017

(30) Foreign Application Priority Data
Aug. 20, 2015 (MX) ................. 2015010792

(51) Int. Cl.
*G01N 33/20* (2019.01)
*C12Q 1/04* (2006.01)
*C12M 1/00* (2006.01)
*G01N 17/00* (2006.01)
*C12M 1/12* (2006.01)
*C12Q 1/06* (2006.01)

(52) U.S. Cl.
CPC ............. *G01N 33/20* (2013.01); *C12M 29/10* (2013.01); *C12Q 1/04* (2013.01); *C12Q 1/045* (2013.01);
(Continued)

(58) Field of Classification Search
CPC ..... G01N 33/20; G01N 17/006; C12M 25/02; C12M 29/10; C12M 29/18; C12M 47/10; C12Q 1/04; C12Q 1/045; C12Q 1/06
See application file for complete search history.

(56) References Cited

U.S. PATENT DOCUMENTS

| | | | | |
|---|---|---|---|---|
| 4,945,758 A | * | 8/1990 | Carpenter | E21B 41/02 73/86 |
| 5,128,100 A | * | 7/1992 | Hollis | C02F 1/50 210/696 |

(Continued)

FOREIGN PATENT DOCUMENTS

EP    2 229 959 A2    9/2010

OTHER PUBLICATIONS

Standard Practice of Preparing, Cleaning, and Evaluating Corrosion Test Specimens[1]—Designation: G1-90 (Reapproved 1999), America Society for Testing and Materials, Reprinted from the Annual Book of ASTM Standards, Copyright ASTM, pp. 1-7.
(Continued)

*Primary Examiner* — Michael L Hobbs
(74) *Attorney, Agent, or Firm* — Dickinson Wright PLLC

(57) ABSTRACT

A portable, single-phase bioreactor provides the in situ study of mesophilic and thermophilic corrosion inducing microbial biofilms on metal surfaces by oil, chemical, petrochemical, oil refining, food, metallurgical, paper fluids. The bioreactor is a batch-type for turbulent and piston-driven laminar flow, operated by cycles, with continuous circulation of the fluid. A culture medium or industrial or production fluid containing microbiota is introduced into a homogenizing container. The bioreactor includes a support section having removable corrosimetric test coupons that contact the fluid under dynamic conditions corresponding to fluid-carrying pipelines, and promote the formation of the microbial biofilm for analysis of the kinetics of microbial biofilm
(Continued)

development. The bioreactor produces turbulence to homogenize the fluid and maintain a temperature of 20 to 80° C. for the microorganism growth. The fluid has a salinity of 2 to 200 ppm (NaCl) and a pH of 2 to 10.

18 Claims, 5 Drawing Sheets

(52) U.S. Cl.
CPC ........... *G01N 17/006* (2013.01); *C12M 25/02* (2013.01); *C12Q 1/06* (2013.01)

(56) References Cited

U.S. PATENT DOCUMENTS

| | | | |
|---|---|---|---|
| 8,388,844 B2 | 3/2013 | Marsolek et al. | |
| 2006/0096917 A1* | 5/2006 | Rose | C02F 3/006 210/614 |
| 2012/0085452 A1* | 4/2012 | Thompson | G01N 17/043 138/44 |

OTHER PUBLICATIONS

J.W. Costerton et al., Bacterial Biofilms: A Common Cause of Persistent Infections, Microbes, Immunity, and Disease, May 21, 1999, vol. 284, Science, www.sciencemag.org, pp. 1318-1322.

Brigitte Carpentier and O. Cerf, Biofilms and Their Consequences, with Particular Reference to Hygiene in the Food Industry, Journal of Applied Bacteriology 1993, 75, 499-511.

NACE International, Standard Recommended Practice, Preparation, Installation, Analysis, and Interpretation of Corrosion Coupons in Oilfield Operations, NACE Standard RP0775-2005, Item No. 21017, 19 pages.

NACE International The Corrosion Society, Standard Test Method, Laboratory Corrosion Testing of Metals, NACE Standard TM0169-2000, Item No. 21200, 13 pages.

* cited by examiner

BIOREACTOR FOR THE IN SITU STUDY OF MICROBIAL BIOFILMS INDUCING CORROSION ON METAL SURFACES

This application claims the benefit under 35 USC § 119 of Mexican application Mx/a/2015/010792 filed Aug. 20, 2015, which is hereby incorporated by reference in its entirety.

TECHNICAL FIELD

The present invention is directed to a bioreactor and method for the in situ study of mesophilic and thermophilic microbial biofilms, inducing corrosion on metallic surfaces.

The bioreactor of the present invention is a portable device that is used in any industry, such as oil, chemical, petrochemical, oil refining, food, metallurgical, paper, etc., using microbial reference strains with a culture medium, or the same operation or production fluid from the industry in question containing its own microbiota.

BACKGROUND

Corrosion is an electrochemical process consisting of an anodic reaction, which involves metal ionization or oxidation (corrosion reaction), and a cathodic reaction based on the reduction of chemical species, causing deterioration of the metals physical and chemical properties, which in turn accelerates its aging and destruction.

Bio-corrosion or microbiologically influenced corrosion (MIC) occurs mostly in stagnant conditions or in operations with low or intermittent fluid flow, and represents a serious problem that affects various industries. There are no official figures on the cost caused by MIC, but an indication of its importance can be obtained from individual companies or industrial sectors.

MIC is an electrochemical process in which microorganisms cause the deterioration of a material, usually a metal, either directly or indirectly, due to their production of extracellular polymeric substances (EPS), organic and inorganic acids and volatile compounds such as ammonia or hydrogen sulfide.

Microorganisms promote electrochemical oxidation reactions and reduction of sulfates, sulfites, nitrates and sulfur in the presence of an electrolyte where there is oxygen consumption by microbial communities, causing cathodic depolarization of the metal.

The corrosion type and rate caused by microorganisms is dependent directly on the availability of adequate nutrients in the environment.

Pitting corrosion on metal surfaces is the corrosion type most associated with microbial activities.

There are various types of microorganisms involved in the processes of metal bio-corrosion. The bacteria commonly associated with these processes are sulphate reducing bacteria (SRB), metal reducing bacteria, sulfide oxidizers, secretors of organic acids and extracellular polysaccharides (EPS).

Biofilms

A biofilm is a microbial mass made of bacteria, fungi, algae and other microorganisms, which usually forms in four stages:
1. Conditioning—the surface for adhesion of pioneer microorganisms is conditioned;
2. Adhesion—the adhesion of pioneer bacterial species and their reproduction takes place, and colonization begins;
3. Colonization—the colony of microorganisms is created and extracellular polymeric substances (EPS) are produced, favoring the formation and growth of the biofilm;
4. Accumulation—the biofilm is fully developed, forming a differential aeration zone between the biofilm and the metal surface through mechanisms of polymer-metal interactions.

The extracellular polymeric substances (EPS) are polysaccharides derived from Gram-negative and Gram-positive cells. They promote the initial adhesion of microorganisms to solid surfaces, the formation and maintenance of biofilms, resistance to environmental factors and allow microorganisms to capture nutrients.

A biofilm is a microbial cell community structure, which produces matrix exopolymers. They inhabit regions between oxic and anoxic layers, and these adhere to both inert or living material. (Costerton et al, "Bacterial Biofilms: A Common Cause of Persistent Infections", Science (www.sciencemag.org), 21 May 1999, Vol. 284, 284. 1318-1322). (The concept of a biofilm, which involves the term microbial communities, comes from B. Carpentier and O. Cerf in "Biofilms and Their Consequences, particularly with reference to hygiene in the food industry," Journal of Applied Bacteriology 1993, 75, 499-511: "a community of microorganisms embedded in an organic polymer matrix, adhering to the surface").

For bacteria to survive and reproduce successfully in many systems, they require the colonization of a surface and/or integration into a community that has formed a biofilm.

In an aqueous system, a microorganism is subject to various forces such as gravity and fluid drag force, which is proportional to the speed with which it moves. Gravity facilitates their transport and bond with the surface.

Once the microorganism has been transported to the substrate surface, initial binding takes place. This is described as a two phase event:
1) Reversible binding phase
2) Irreversible binding phase.

Adhesion is the principle stage, in which a bacterium performs surface colonization. This colonization increases with increasing surface roughness, since there is a greater surface area and the separation forces decrease.

It is important to note that a key element to achieve biofilm formation is that the flow in which it is growing is in the laminar regime, so that it does not detach from the surface to which it is adhered.

Hydrodynamics also plays an important role in the biofilm development, as these organizations develop on a liquid-solid interface where the flow speed that passes across it influences the microorganism's physical detachment. The biofilms also possess a canal system in which water flows, allowing them to transport nutrients, oxygen and waste.

In order to study adhesion of microorganism such as bacteria and their biofilm formation under flow conditions, laboratory model systems have been used, the design of which results in bioreactors working under the desired conditions.

The maximum number of attached bacteria per square centimeter is a parameter that allows one to characterize and determine the biofilm formation dynamics, which can be much slower and proportionally lower in a discontinuous and turbulent system than in a laminar flow system. The biofilm formation rate and thickness are not as dependent on the carbohydrates availability (glucose or lactate) or degree of consumption of any substrate, as they are on iron salts. The number of bacteria on the surface is influenced by the presence of other bacterial species, which reduces the number of cells in the biofilm. The number of bacteria on the surface is quantified in order to evaluate the influence of environmental factors on adhesion and biofilm formation using a combination of fluorescence, atomic force and environmental scanning microscopy, ultrasonic surface bacteria remover and indirect conductimetry.

RELATED PATENT DOCUMENTS

The closest state of the art related to the present invention, which can be referred to as the method or device for the study, evaluation or characterization of biofilms under different conditions and various factors, are represented by the following patent documents:

In the patent application EP 2,229,959 A2, published on Sep. 22, 2010, Daniel Fäh et al., refer to the study of monospecific or pluri-specific biofilms (*Pseudomonas, Staphylococcus, Mycobacterium, Micrococcus, Rhodococcus, Cellulosimicrobium, Microbacterium, Williamsia, Enterobacteriacae, Streptococcus, Enterococcus, Leptospira, Clostridium, Listeria, Legionella, Salmonella, Campylobacter, Citrobacter, Shewanella, Bulkholderia, Serratia, Comamonas, Cryptococcus, Rhodotorula, Candida, Saccharomyces, Penicillium* and *Cladosporium*), to qualitatively and quantitatively measure the biocides efficiency, with applications in medicine, water treatment, cleaning and food handling. The reactor has a rail for interchangeable supports (coupons) for biofilm growth, aeration through a pump, metal plate with openings connecting to an external environment. Openings to remove the biofilm support rails. Up to 18 cylindrical supports (coupons) can be used simultaneously. Most of the coupon surface is exposed to the fluid. Continuous culture possible. Aeration container. Possibility of running a blank. Use of dyes in situ and ex situ. EPS detection and microscopic techniques. It has a fluid outlet, metal or polypropylene rails, and uses metal coupons with the possibility of combining different material coupons. Biomass does not settle and the fluid is constantly renewed. In the configuration of this reactor:

There is no fluid recirculation, it must be constantly renewed;

The system requires three pumps and an air compressor;

It does not ensure the right mix of substrate and microorganism;

It ensures the biofilm growth is generated only through specific culture media; there is no testing with liquid media, from waste products of general industry nor specifically from the oil industry;

It is not possible to raise the fluid temperature to modify the biofilm development conditions;

It does not have a site for the entry of a thermometer or electrodes for measuring environmental parameters or for taking liquid or gas samples; and There is no method to agitate or cause turbulence to mix the medium.

In Patent U.S. Pat. No. 8,388,844 B2, granted on Mar. 5, 2013, Michael Marsolek and Bruce E. Rittmann refer to the development of a reactor that considers water coming from a system of wastewater treatment. This is a configuration with fluidized bed system with particulate material, as a basis for biofilm adherence. Advanced oxidation is promoted by introducing gas and TiO. The reaction chamber has multiple water and gas inputs and outputs. The configuration does not consider the use of coupons of any material. It is possible to perform continuous inoculation. Aeration occurs throughout the reactor. The biofilm promotes the removal of contaminants in treated water. The reactor includes water outlets for continuous sampling. Biomass circulates throughout the reactor and water is constantly renewed. It recirculates fluid (only through a mechanical stirrer). It includes a radiation source (UV-Vis). An air compressor is used. There is agitation and the correct mixture of substrate and microorganism is ensured. The biofilm is created and protected by the porosity of the fluid bed. In the reactor configuration:

The fluid type is not specified;

The use of coupons of any material type is not considered;

The biofilm does not detach (because it is attached to the fluid bed);

It is no possible to heat the fluid; and

It does not consider temperature measurement for mesophilic or thermophilic process.

SUMMARY OF THE INVENTION

The state of the art known by the applicant, mainly represented by the technologies described in patent documents referred, to above differs technically and it is clearly exceeded by the present invention. The state of the art device does not refer to a bioreactor for the in situ study of mesophilic and thermophilic microbial biofilms, inductors of corrosion on metal surfaces. The bioreactor of the invention is a portable device that can be used in any industry, such as, but not limited to oil, chemical, petrochemical, oil refining, food, metallurgical, paper, etc., using microbial reference strains with a culture medium, or the same operation or production fluid from the industry in question containing its own microbiota.

It is therefore the objective of the present invention to provide a bioreactor for the in situ study of mesophilic and thermophilic microbial biofilms that influence the corrosion on metal surfaces. The bioreactor is a "batch" portable device, which handles both turbulent and piston-driven laminar flow, operation in cycles, with continuous fluid circulation at a temperature of 20 to 80° C., salinity from 2 to 200 ppm (NaCl) and a pH range of 2 to 10, physical and hydrodynamic conditions necessary to promote the growth of mesophilic or thermophilic microorganisms and the formation microbial biofilms developing from their initial stages to mature stages.

Another objective of the present invention is to provide a bioreactor for the in situ study of mesophilic and thermophilic microbial biofilms, formed with a reference bacterium or bacterial consortium (several reference microbial strains) and a culture medium or the same industrial operation or production fluid that contains its own microbiota.

Yet another objective of the present invention is to provide a bioreactor and method for the in situ study of mesophilic and thermophilic microbial biofilms, which preferably uses a culture medium and a reference bacterium (mono-specific biofilm), a consortium of reference bacteria (multi-specific biofilm), mixed cultures isolated from industrial operation or production fluids, or the same industrial operation or production fluids containing their own microbiota (multi specific biofilm typical of the test fluid), since the system is completely sealed and prevents contamination from external microorganisms.

The features of the invention are basically attained by providing a bioreactor for the in situ study of corrosion inducing mesophilic and thermophilic microbial biofilms on metal surfaces, comprising: a homogenizing container (1) of a culture medium or industrial operation or production fluid, which has multiple inputs (2); a flexible conduit (3) that transports the fluid from the homogenizing vessel (1) to a hermetic container (4) with a pump and thermostat; a flexible conduit (5) which carries the fluid pumped from the airtight container (4) to the corrosimetric test coupons support section (6), which has an intake/injection port (7), hermetic holders for corrosimetric test coupons (8) a corresponding space for corrosimetric test coupon's insertion/removal (9) and a key (10); and a settling vessel (11) which receives the flow with biomass waste residuals from the test coupons support section (6), and which has a key for purification (12).

The features of the invention are further attained by providing an in situ method for detecting and measuring the formation of biofilm and the presence of mesophilic and thermophilic microorganisms present in a fluid that forms microbial biofilms on metal surfaces using the bioreactor of the invention. The method of the invention introduces the fluid containing the microorganism into the bioreactor and analyzes the fluid for the presence of the microorganism.

DETAILED DESCRIPTION OF THE INVENTION

Figure 1:
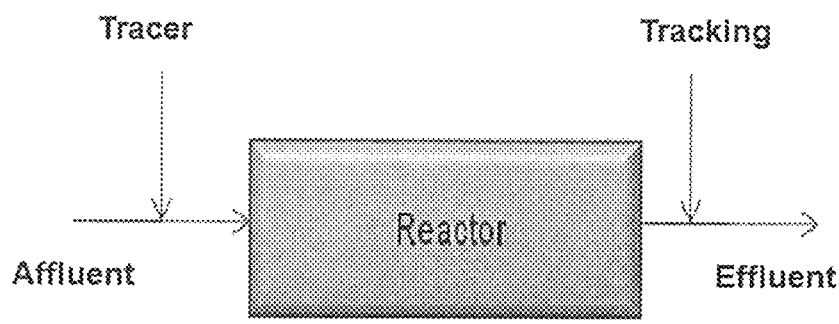
FIG. 1 shows how the selection tests for a tracer or marker (dye) are performed.

The present invention refers to a bioreactor and method for the in situ study of mesophilic and thermophilic microbial biofilms, inducing corrosion on metal surfaces.

The bioreactor of the present invention is a device used in any industry, such as, but not limited to, oil, chemical, petrochemical, oil refining, food, metallurgical, paper, etc.

Among the most important characteristics of the present invention are the following:

1) It allows the in situ study of mesophilic and thermophilic microbial biofilms on corrosimetric test coupons commonly used in monitoring and evaluation of corrosion in the field or industrial activities, preferably in pipes and ducts that carry industrial operation or production fluids, such as wastewater or produced water. The bioreactor of the present invention is a device that can be used in any industry, such as oil, chemical, petrochemical, oil refining, food, metallurgical, paper, etc.

2) The configuration of the bioreactor is of the "batch" type. The bioreactor handles both turbulent and piston-driven laminar flow, in operation cycles, with a continuous circulation of the fluid. The bioreactor employs microbial reference strains with a culture medium or the same industrial operation or production fluid, containing its own microbiota, which is introduced into the load of the receiving body; the bioreactor is single phase.

3) The bioreactor preferably uses a culture medium and a reference bacterium (mono-specific biofilm), a consortium of reference bacteria (multi-specific biofilm), mixed cultures isolated from industrial operation or production fluids, or the same industrial operation or production fluid containing their own microbiota (multi-specific biofilm typical of the test fluid), since the system is completely sealed and prevents contamination from external microorganisms.

4) The bioreactor comprises a support section for corrosimetric test coupons, where the corrosimetric test coupons are in contact with the fluid in dynamic conditions, such as those found in fluid carrying pipelines, naturally promoting the formation of a microbial biofilm. Every so often the corrosimetric test coupons are removed for analysis and thus follow the kinetics of microbial biofilm development. The supports for corrosimetric test coupons are at different angles with respect to the longitudinal axis of the tube, permitting analysis of the corrosimetric test coupons under different adhesion conditions of the microbial biofilm.

5) The bioreactor operates at the physical and hydrodynamic conditions required for the formation of a mature microbial biofilm. In particular, the bioreactor takes into account that the flow must be laminar in the corrosimetric test coupon's support section in order to promote the microorganism's growth and the microbial biofilm's formation and development, from the initial stage to mature stages. The bioreactor comprises a head to decrease the flow rate and obtain a piston-driven laminar flow in the section where the microbial biofilm forms, resembling the physical and hydrodynamic conditions that occur in pipelines carrying industrial fluid, for proper mass transfer. The operating conditions of the bioreactor comprise a section in which there is sufficient turbulence for the fluid to homogenize and maintain a temperature of 20 to 80° C. necessary for growth of the mesophilic or thermophilic microorganisms, salinity from 2 to 200 ppm (NaCl) and a pH range of 2 to 10. In other words, the bioreactor's operating conditions are adjustable to the physicochemical characteristics of the fluid from the industry to be assessed.

6) The bioreactor is portable, so it can be installed in the same place where monitoring and control of corrosion induced by microorganisms is carried out, or as close or as far away as desired.

Data and Theoretical Formulae

The bioreactor's design basis lies in the calculations of the receiving body's volume and length, in the length to diameter ratio, and, primarily, in the standard characteristics required for biofilm formation, (pH and optimum temperature for growth and laminar flow regime).

For the bioreactor design and construction, the following points were considered:

The types of pipes, coplex, connectors, reducers, elbows, receiving body, settler, keys for sampling, serpentines, hydraulic pump, container with resistance; steel coupons; copper terminals; hoses; etc Theoretical data for the design of bioreactors.

Mathematical formulae for the design:

Determination of pipe's diameters, taking into account the relation:

$L/D=3/1$

Where:
L=length (m)
D=diameter (m)

Flow rate determination from the Reynold's number in the laminar regime (zone where coupons are inserted). For a fluid flowing through an upright circular pipe, the Reynold's number is given by:

$$Re = \frac{\rho v_s D}{\mu}$$

or equivalently by:

$$Re = \frac{v_s D}{\upsilon}$$

where:
$\rho$=fluid density (kg/m$^3$)
$v_s$=fluid characteristic velocity (m/s)
D=pipeline diameter, through which the fluid flows, or the system's characteristic length (m)
$\mu$=fluid dynamic viscosity (kg/ms)
$\upsilon$=fluid kinematic viscosity (m$^2$/s)

$$\upsilon = \frac{\mu}{\rho}.$$

Determination of the volumetric flow rate of the pipe:

$Q = v*A$

Where:
Q=volumetric flow rate (m$^3$/s)
v=liquid velocity (m/s)
A=pipe area (m$^2$)

Determination of de sedimentation rate in the sedimentation tank (Stokes law):

$$Vs = \frac{1}{18}g\left(\frac{\rho_s - 1}{\eta}\right)d^2$$

Where:
$V_s$=particle fall velocity (m/s)
g=acceleration due to gravity (m/s$^2$)
$\rho_s$=sedimented particle's density (kg/m$^3$)
$\eta$=fluid viscosity (kg/ms)
d=particle diameter (m)

Determination of sedimentation tank dimensions:

$A = 2\pi r H = Q/Vs$ where:
A=area (m$^2$)
$\pi$=3.1416
r=radius (m)
H=height or depth (m)
Q=volumetric flow rate (m$^3$/s)
Vs=particle fall velocity (m/s)

Required pump power $$P_{teorica} = H_B \times \rho \times g \times Q_T$$

$$P_{real} = \frac{P_{teorica}}{(\%)}$$

Where:
%=efficiency
$H_B$=dynamic height (workload of the pump) (m)
d=density of water (kg/m$^3$)
g=acceleration due to gravity (m/s$^2$)
Q=volumetric flow rate (m$^3$/s)

Evaluation of the results for the bioreactor design, performing the staining test and applying the Simpson model for numerical integration in order to determine changes in hydraulic retention times during operation and the actual flow rate.

Choosing a tracer or marker (dye) with stable behavior during spectrophotometric techniques, as shown in FIG. 1

1) For each sample obtained, the absorbance was determined using a UV-VIS spectrophotometer.
2) With this, the pattern response curve was obtained "time vs. concentration".
3) Obtaining diagram curves C, which provide the theoretical time for distribution to the reactor outlet (sampling after the zone where the coupons are inserted).

Figure 2:
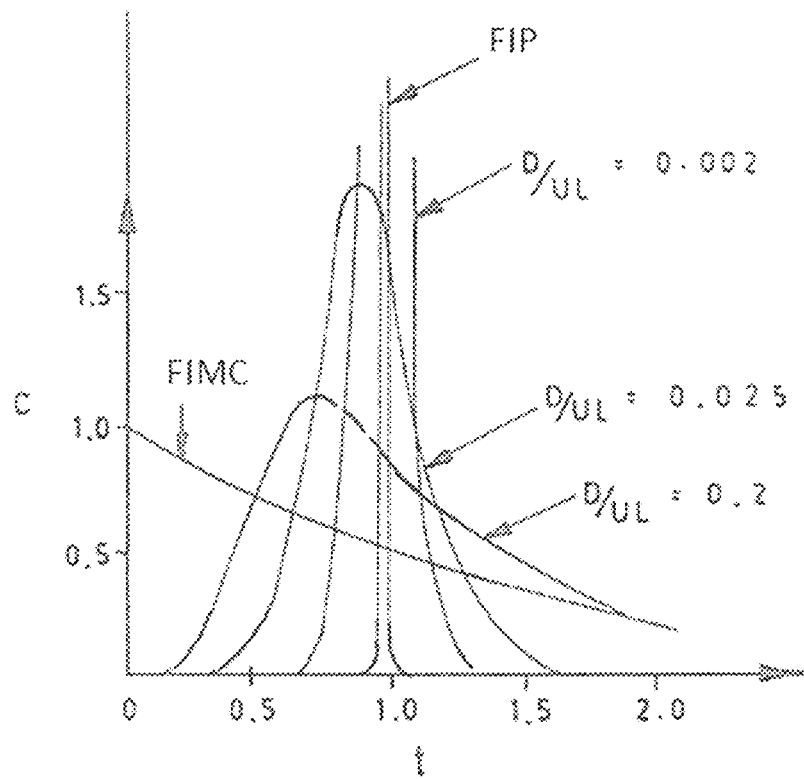
FIG. 2 shows diagram curves C characteristic for different reactors types, where:
FIP=Ideal piston-driven flow, and
FIMC=Ideal flow for complete mixing.

FIG. 2 shows the diagram curves C, which are characteristic for each different reactor type, where the axes are dimensionless and given by $C/C_0$ vs $t/t_0$, where:
C=sample concentration in the sampler.
$C_0$=concentration if the discharged tracer dose is uniformly mixed throughout the coupon section.
t=actual sampling time after adding the tracer.
$t_0$=theoretical hydraulic retention time ($t_0$=V/Q).

4) The Simpson numerical integration model was applied to determine the prevailing flow type in the coupon area, in which the result of the marker or dye test in terms of the dimensionless expression D/UL was ascertained. This is known as the "dispersion number" and it is commonly used to characterize different reactors types.

Where:
D/UL=Simpson axial dispersion number or module (dimensionless)

D=dispersion coefficient (m²/s)
U=fluid linear velocity (m/s)
L=reactor's length (m)

5) When it is indicated that the flow behavior is laminar, the bioreactor dimensions are appropriate.

Standardizing the Bioreactor

During the standardizing stage of the bioreactor's operation, the corrosimetric test coupons were prepared, cleaned and evaluated under the following protocol, which are incorporated by reference in their entirety:

ASTM G 1-90 *Standard Practice for Preparing, Cleaning, and Evaluating Corrosion Test Specimens;*

NACE Standard TM0169. *Standard Test Method—Laboratory Corrosion Testing of Metals;* and NACE Standard RP0775. Standard Recommended Practice—*Preparation, Installation, Analysis, and Interpretation of Corrosion Coupons in Oilfield Operations.*

Through the gravimetric method, by considering the corrosion rate measured from the material loss from the corrosimetric test coupon surface per unit time, referred to as mils per year (mils-per-year (mpy)). (One mil is a thousandth of an inch (0.001"); such units are common in monitoring programs and corrosion control in various industries.)

The treated and cleaned corrosimetric test coupons were weighed and installed in the bioreactor's corrosimetric test coupon's support section, for microbial biofilm formation under aseptic conditions.

The bioreactor operation was performed with a bacterial strain, isolated from oil produced water, identified as IMP-SW, (this is a Gram-negative, facultative bacterium which does not form spores, and reduces metals such as iron and is associated with MIC). The device operation was carried out in a culture medium with a salinity of 30 g/l (NaCl) as a flowing medium, a pH 7 and a temperature of 30° C. The bioreactor operated for six months, during which, every fortnight, samples of each corrosimetric test coupon were taken. These were replaced each time with new corrosimetric test coupons, generating specific data for adhesion, formation and growth times of microbial biofilm. The microbial biofilm growth and the biocorrosion process were confirmed by descriptive studies in test coupons, using environmental scanning electron microscopy with X-ray spectroscopy (EDS) and the gravimetric method to assess the material loss from the coupons.

Once the best working conditions were understood and established, the bioreactor was operated with the IMP-SW bacteria for 1.450 hours in a culture medium with a salinity of 30 g/l (NaCl) and a temperature of 30° C. This permitted growth of the microbial biofilm up to its mature state (FIG. 6) so that its effects on the corrosimetric test coupon's surface at the end of this time period could be recorded. The results obtained from the gravimetric method are presented in Table 1.

Figure 3:
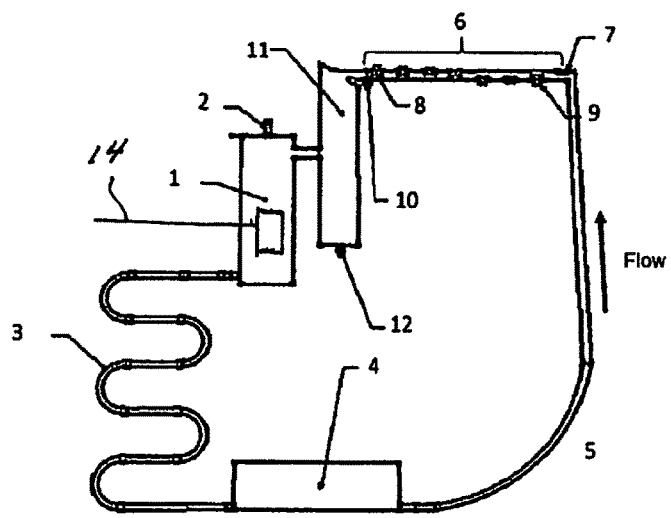
FIG. 3 is a general outline of the bioreactor and its components in the present invention.

The general scheme of the bioreactor of the present invention and its components are shown in FIG. 3. The flow of the culture medium or the operation or production fluid from the industry to be assessed has a counterclockwise orientation. The bioreactor comprises a homogenization vessel (1), with a multiple input (2) for:

Pouring in the culture medium or operation/production fluid from the industry to be assessed.

Sampling fluids or gases generated using a sterile syringe through a septum, and Measuring physicochemical parameters such as temperature, salinity, oxygen concentration, pH and conductivity, by employing submergible electrodes 14.

A flexible conduit (3) is responsible for transporting the fluid from the homogenization vessel (1) into a hermetic container (4) with a pump and thermostat to maintain the desired temperature throughout the system.

The fluid in the hermetic container (4) is pumped through a flexible conduit (5), towards the corrosimetric test coupon's support section (6). There, the fluid flow becomes piston-driven laminar flow for microbial biofilm formation. At one end of this, there is an intake/injection port (7) through which fluid samples are taken; or substances such as biocides, corrosion inhibitors or scale removers, are injected to observe their effect on microbial biofilm development. Throughout this section, hermetic holders (preferably seven) for the corrosimetric test coupons are embedded (8) with different spatial orientation and angle, each of them with its corresponding space for insertion/removal of a corrosimetric test coupon (9), on the far left part of this section there is a key (10) which allows one to block the flow to operate independently the sedimentation (11) and the homogenization containers (1) when the system is off; after the test coupon support section (6) for the microbial biofilm formation, the flow is led to a settling vessel (11), which receives potential biomass waste that is generated when microbial biofilms are mature enough, this container has a purification key (12), which allows draining the container when required.

Figure 4:
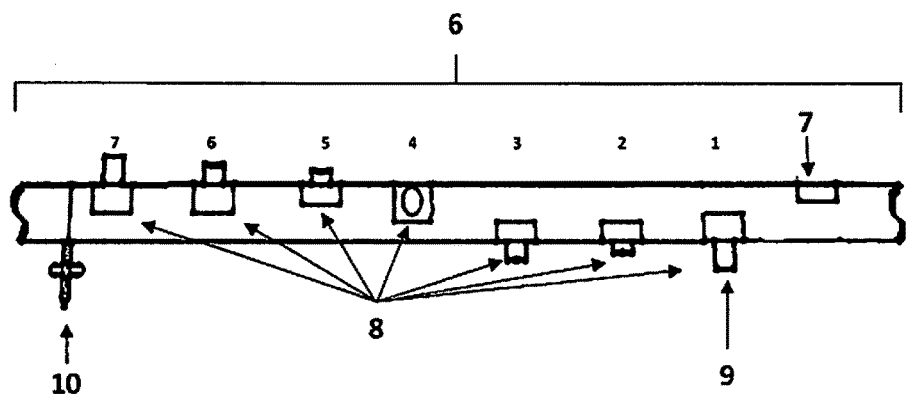
FIG. 4 shows an amplified section of the support for corrosimetric test coupons, for the formation of microbial biofilms.

The test coupon's support section (6), where the microbial biofilms form, is illustrated in FIG. 3 and amplified in FIG. 4, and is one of the most important parts of the bioreactor. This is because in this section, the development of the microorganisms takes place on the test coupon's surfaces. Each of them is fastened with a kind of jacket which serves as hermetic holder. The corrosimetric test coupon holders, preferably seven of them, are distributed at different distances and spatial positions within the light pipe through which the test fluid flows. With this design, the microbial biofilm development at different angles with respect to the horizontal axis of the piston-driven laminal flow can be observed. Also, one single corrosimetric test coupon can be

TABLE 1

Results obtained from corrosimetric test coupon corrosion, which were installed in the bioreactor of the present invention, by the gravimetric method using a bacterial strain isolated from oil produced water, identified as IMP-SW, for 1.450 hours.

| | Corrosimetric coupon | | | | | | |
|---|---|---|---|---|---|---|---|
| | 7 | 6 | 5 | 4 | 3 | 2 | 1 |
| Corrosion rate (mpy) | 3.53 | 5.81 | 8.73 | 9.22 | 9.86 | 10.08 | 10.09 |
| Corrosion Classification (qualitative) | Moderate | Severe | Severe | Severe | Severe | Severe | Severe | extracted without affecting the others, therefore making it easier to analyze it individually.

The corrosimetric test coupon's support section (6) for microbial biofilm formation can be dismounted independently from the whole system.

Similarly, the three vessels of the system are removable for cleaning and sterilization, as well as the rest of the conduits.

EXAMPLE

A practical example of the present invention is presented below, for a better understanding of said invention, without limiting its scope.

Example 1

Corrosimetric test coupons were prepared, cleaned and evaluated, following protocols ASTM G 1-90, NACE Standard TM0169 and RP0775, through the gravimetric method.

The cleaned and processed corrosimetric test coupons were weighed and installed in the bioreactor's coupon support section, ready for microbial biofilm formation, under aseptic conditions.

The bioreactor was operated using oil industry produced water as the fluid, at 42° C. This procedure was performed in duplicate, i.e. in two runs; the operating time was 1,450 hours for each. Subsequently, the corrosimetric test coupons were removed and treated for cleaning and evaluation, as described in the protocols above.

The corrosimetric test coupons were observed using an environmental scanning microscope with and without a biofilm.

The characteristics of the oil industry production water used were the following: 118 g/L NaCl, pH=7.1, temperature of 42° C. in situ (sampling site). It is worth noting that the microorganisms that formed the corrosive multi-species microbial biofilm are native; they are microorganisms that commonly inhabit the produced water used in the oil industry.

The results for corrosion rate (mpy) of the corrosimetric test coupons installed in the bioreactor of the present invention, obtained through the gravimetric method and using oil industry produced water, are shown in Table 2. An experiment time of t=1.450 hours applied to each.

In this regard, it is important to reiterate that 14 corrosimetric test coupons were tested in two separate operation runs.

A mature microbial biofilm was formed in all of the corrosimetric test coupons, which was removed for cleaning and gravimetric evaluation of the material lost during the process.

Figure 5:
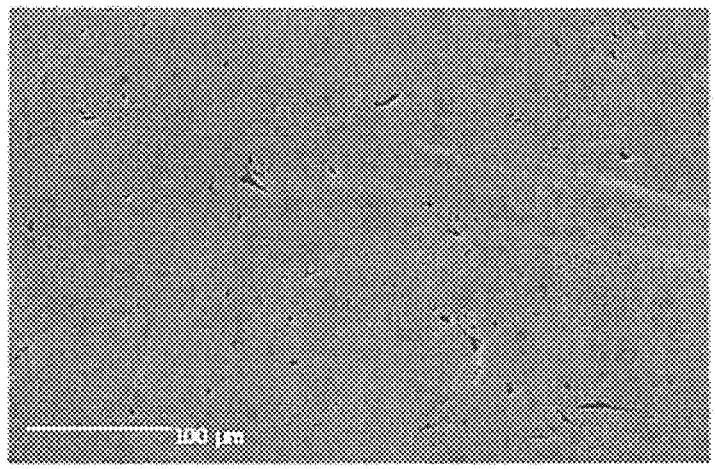
FIG. 5 is a micrograph obtained by scanning electron microscopy of a representative corrosimetric test coupon representative of the Example 1, before being installed (initial surface-time t=0 hours).
Figure 6:
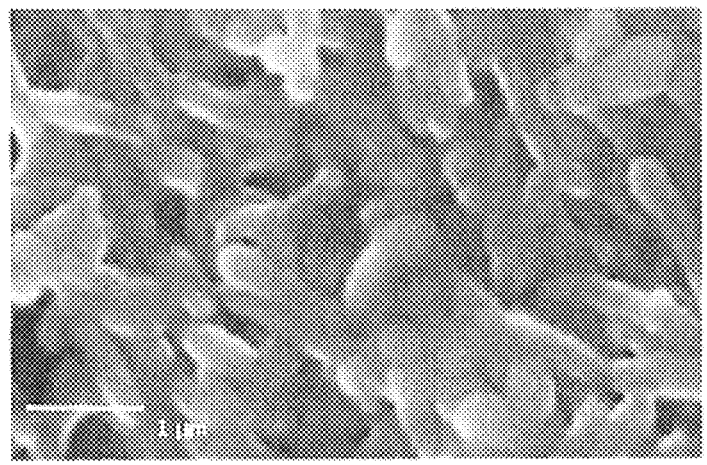
FIG. 6 is a micrograph obtained by scanning electron microscopy of a corrosimetric test coupon with microbial biofilm with the IMP-SW bacterial strain, isolated from produced water of oil industry (surface with microbial growth-at t=1.450 hours' bioreactor operation time).
Figure 7:
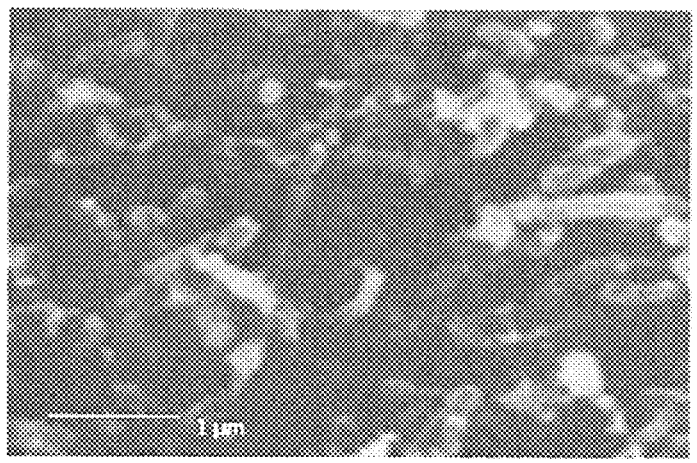
FIG. 7 is a micrograph obtained by scanning electron microscopy of a corrosimetric test coupon representative of the Example 1, at the end of the bioreactor's operation with produced water of oil industry (surface with microbial growth-at t=1.450 hours' bioreactor operation time).
Figure 8:
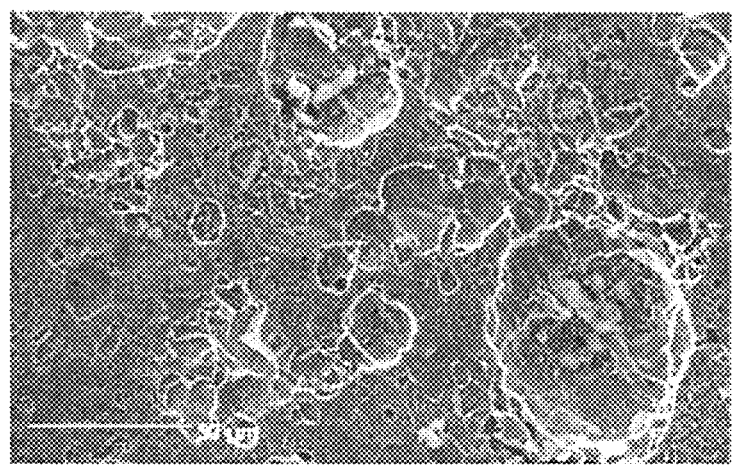
FIG. 8 is a micrograph obtained by scanning electron microscopy of a representative corrosimetric test coupon, after having had the microbial biofilm removed (metal surface pitting generated by microbial biofilm).

Micrographs obtained by scanning microscopy of the corrosimetric test coupons before installation are shown in FIGS. 5 to 8 (FIG. 5 shows the initial surface–at t=0 hrs); and with the microbial biofilm formed when using oil industry production water (FIGS. 6 and 7 show the surface with microbial growth, after 1.450 hours of bioreactor operation). Finally, a micrograph obtained by scanning electron microscopy of the corrosimetric test coupons after removal of the microbial biofilms is shown in FIG. 8 (pitting of the metal surface generated by a microbial biofilm after biofilm removal).

Figure 9:
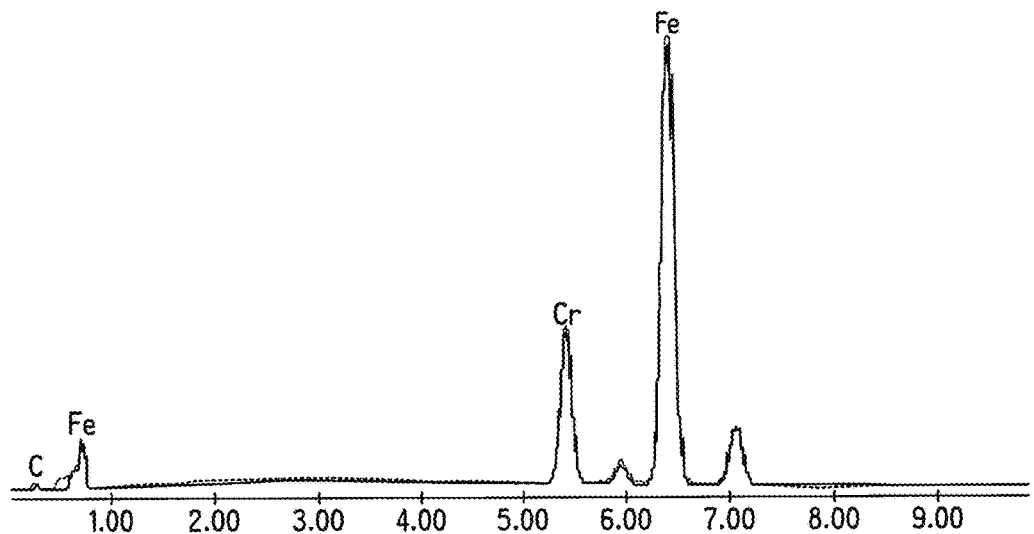
FIG. 9 is a spectrum obtained by X-ray spectroscopy (EDS) of five points on the surface of a corrosimetric test coupon, representative of the Example 1 before bioreactor operation-at time t=0 hours.
Figure 10:
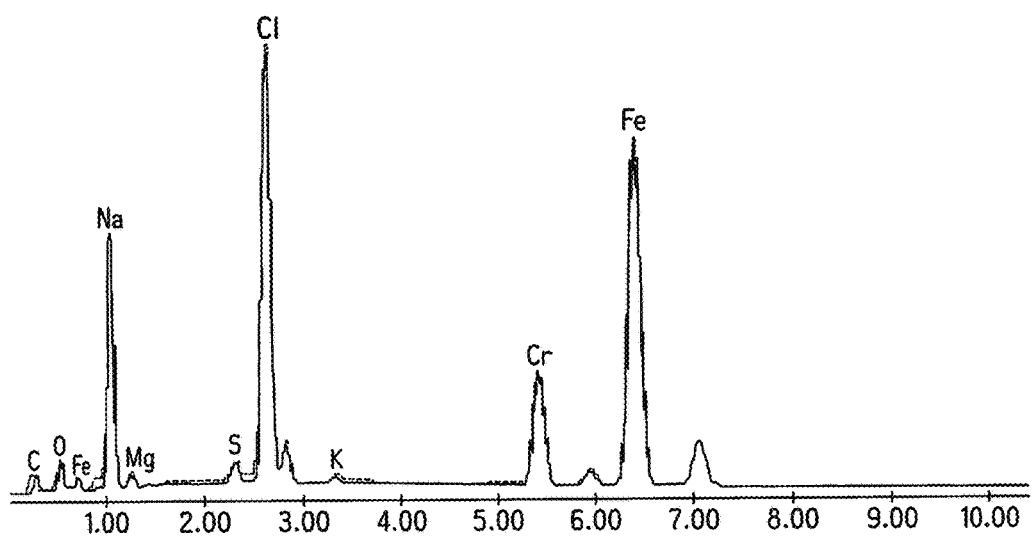
FIG. 10 is a spectrum obtained by X-ray spectroscopy (EDS) of five points on the surface of a corrosimetric test coupon, representative of the Example 1, after bioreactor operation-at time t=1.450 hours.

The spectra of five points obtained by X-ray spectroscopy (EDS) on a test coupon surface is shown in FIGS. 9 and 10. Before activating the bioreactor at t=0 hours (FIG. 9) and after the bioreactor's operation at t=1,450 hours (FIG. 10).

What is claimed is:

1. A bioreactor for the in situ study of corrosion inducing mesophilic and thermophilic microbial biofilms on metal surfaces and measuring a rate of corrosion of a surface of a metal test coupon, said bioreactor comprising:
   a homogenizing container (1) containing a culture medium, industrial fluid or production fluid, said homogenizing container having an inlet arid an outlet;
   a hermetic container having a thermostatic temperature control and pump, an inlet and an outlet;
   a first flexible conduit (3) connected to said outlet of said homogenizing container for transporting said fluid from said homogenizing container (1) to said inlet of said hermetic container (4);
   a support container for supporting a plurality of test coupons, said support container having substantially tubular shaped wail with an inner perimeter surface forming a longitudinal passage, a fluid inlet at an inlet end of said longitudinal passage, and fluid outlet at an outlet end of said longitudinal passage,
   a second flexible conduit (5) connected to said outlet of said hermetic container and to said fluid inlet of said support container to carry fluid pumped from the hermetic container (4) to the support section (6),
   a plurality of hermetic holders extending through said wall and removably coupled to said wall of said support container, each hermetic holder supporting a corrosimetric metal test coupons (8) in said longitudinal passage of said support section, said hermetic holders and corrosimetric metal test coupons being longitudinally spaced apart along a longitudinal axis of said longitudinal passage, and angularly spaced apart around a circumference of said inner perimeter surface of said longitudinal passage of said support container; and

TABLE 2

Corrosion rate (mpy) of the corrosimetric test coupons installed in the bioreactor of the present invention, through the gravimetric method, using oil industry produced water, and a run time of t = 1,450 hours.

|  | Corrosimetric coupon | | | | | | |
| --- | --- | --- | --- | --- | --- | --- | --- |
|  | 7 | 6 | 5 | 4 | 3 | 2 | 1 |
| Corrosion rate (mpy) (run operation 1) | 24.02 | 22.11 | 43.65 | 42.64 | 45.42 | 36.93 | 43.42 |
| Corrosion rate (mpy) (run operation 2) | 24.53 | 23.87 | 47.00 | 42.80 | 44.71 | 35.65 | 44.00 |
| Corrosion Classification (qualitative) | Very severe | Very severe | Very severe | Very severe | Very severe | Very severe | Very severe | a settling container (11) having an inlet with a valve connected to said outlet of said support section for receiving fluid and biomass waste residuals from the support section (6), said settling vessel having an outlet connected to said inlet of said homogenizing container forming a closed loop, said settling vessel having a drain for removing sediment form said settling container.

2. The bioreactor of claim 1, wherein the bioreactor is a batch portable device providing turbulent and piston-driven laminar flow through said support container, continuous flow in operation cycles, and continuous fluid circulation at temperatures of 20 to 80° C., salinity from 2 to 200 ppm (NaCl) and a pH in the range 2 to 10.

3. A bioreactor according to claim 1, wherein said culture medium or industrial or production fluid, includes a culture medium and a reference bacterium (monospecific biofilm), a consortium of reference bacteria (multi-specific biofilm), isolated mixed cultures of industrial or production fluids, or an industrial or production fluid from an assessed industry containing microbiota.

4. A bioreactor according to claim 1, wherein said inlet (2) of the homogenization container (1) is configured for receiving said culture medium or operational or production fluid from an industry to be assessed.

5. A bioreactor according to claim 1, said homogenization container (1) includes submersible electrodes for the measurement of temperature, salinity, oxygen concentration, pH and conductivity.

6. A bioreactor according to claim 1, said inlet of said support container (6) is configured for injecting biocides, corrosion inhibitors or scale removers to said support container, and removing a fluid sample from said support section.

7. A bioreactor according to claim 1, wherein said corrosimetric test coupons (8) are oriented in different spatial orientations in said corrosimetric test coupons support container (6).

8. A bioreactor according to claim 1, wherein said support container includes seven hermetic holders for a respective corrosimetric test coupons (8), each hermetic holder supporting said respective corrosimetric test coupons at a different spatial orientation and angle in said longitudinal passage of said support container (6).

9. A bioreactor according to claim 1, wherein said valve of said support container (6) is configured to block the flow of fluid from said support container and operate independently said settling containers (11) and homogenization container (1) when the reactor is off.

10. A bioreactor according to claim 1, wherein said corrosimetric test coupons support container (6) are independently removable from said support container.

11. A bioreactor according to claim 1, wherein said valve of the settling container (11) is configured to drain said settling container.

12. A bioreactor according to claim 1, wherein said homogenization container, hermetic container, support section, and settling container are independently removable from each other for cleaning and sterilization.

13. A bioreactor according to claim 1, wherein said fluid is oil, chemical fluids, petrochemical fluids, oil refining fluids, food fluids, metallurgical fluids, and paper fluids.

14. The bioreactor of claim 1, wherein said metal test coupons have a first end coupled to the respective holder and a second end positioned in said longitudinal passage at the inner perimeter surface of said support container, and where said metal test coupons are oriented on said inner perimeter surface to detect a rate of corrosion at the location of said metal test coupons.

15. The bioreactor of claim 1, wherein said first flexible conduit has a serpentine configuration to control the flow of said fluid to said hermetic container.

16. A method of measuring corrosion on a metal surface by a biofilm using the bioreactor of claim 1, said method comprising introducing said fluid containing said culture medium into said homogenization container where said fluid has a temperature of 20 C to 80 C, a salinity of 2 to 200 ppm (NaCl), and a pH of 2 to 10;

carrying said fluid from said homogenizing container through said first flexible conduit to said hermetic container;

carrying said fluid form said hermetic container through said second flexible conduit to said support container;

directing said fluid through said longitudinal passage of said support container into contact with each of said test coupons;

carrying said fluid from said support container to said settling container and continuously carrying said fluid from said settling container to said inlet of said homogenizing container; and removing said test coupons and analysing formation of biofilm and corrosion of said test coupons.

17. The method of claim 16, wherein said fluid is a laminar flow through said longitudinal passage of said support section.

18. The method of claim 15, wherein said fluid is a turbulent flow through said longitudinal passage of said support section.

* * * * *